United States Patent
Artaki et al.

(10) Patent No.: US 9,271,768 B2
(45) Date of Patent: Mar. 1, 2016

(54) ORTHOPEDIC FIXATION DEVICES AND INSTRUMENTS FOR INSTALLATION THEREOF

(71) Applicant: GLOBUS MEDICAL, INC., Audubon, PA (US)

(72) Inventors: Alexander Artaki, Phildadelphia, PA (US); Khiem Pham, Chalfont, PA (US); Matthew Bechtel, Norristown, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 70 days.

(21) Appl. No.: 14/137,157

(22) Filed: Dec. 20, 2013

(65) Prior Publication Data

US 2015/0173807 A1    Jun. 25, 2015

(51) Int. Cl.
*A61B 17/70* (2006.01)
*A61B 19/00* (2006.01)

(52) U.S. Cl.
CPC ......... *A61B 17/7088* (2013.01); *A61B 17/7002* (2013.01); *A61B 17/7037* (2013.01); *A61B 17/7085* (2013.01); *A61B 17/7086* (2013.01); *A61B 17/7089* (2013.01); *A61B 2019/307* (2013.01)

(58) Field of Classification Search
CPC ........... A61B 17/7074; A61B 17/7076; A61B 17/7077; A61B 17/7079; A61B 17/708; A61B 17/7082; A61B 17/7083; A61B 17/7085; A61B 17/7086; A61B 17/7088; A61B 17/7089; A61B 17/7091; A61B 2019/307

See application file for complete search history.

(56) References Cited

U.S. PATENT DOCUMENTS

| | | | | |
|---|---|---|---|---|
| 6,183,472 B1 * | 2/2001 | Lutz | ................... | A61B 17/7032 606/104 |
| 6,440,133 B1 * | 8/2002 | Beale | ................. | A61B 17/7086 606/104 |
| 7,608,081 B2 * | 10/2009 | Abdelgany | ......... | A61B 17/7086 606/103 |
| 7,621,918 B2 * | 11/2009 | Jackson | ............. | A61B 17/7037 606/104 |
| 7,651,502 B2 * | 1/2010 | Jackson | ............. | A61B 17/7086 606/99 |
| 7,887,541 B2 * | 2/2011 | Runco | ................ | A61B 17/7086 606/279 |
| 7,909,830 B2 * | 3/2011 | Frigg | .................. | A61B 17/7002 606/104 |
| 7,947,046 B2 * | 5/2011 | Justis | ...................... | A61B 17/88 606/264 |
| 8,123,785 B2 * | 2/2012 | Weaver | ................. | A61B 17/025 606/272 |
| 8,303,595 B2 * | 11/2012 | Jones | .................. | A61B 17/7086 606/86 A |
| 8,308,774 B2 * | 11/2012 | Hoffman | ............ | A61B 17/7086 606/279 |
| 8,998,922 B2 * | 4/2015 | Rutledge | ............ | A61B 17/7032 606/104 |
| 2008/0015601 A1 * | 1/2008 | Castro | ................ | A61B 17/7086 606/86 R |
| 2012/0271365 A1 * | 10/2012 | Daubs | ................. | A61B 17/7086 606/86 A |
| 2013/0184763 A1 * | 7/2013 | McClintock | ........... | A61B 17/88 606/279 |
| 2014/0039567 A1 * | 2/2014 | Hoefer | .................. | A61B 17/708 606/86 A |
| 2014/0249583 A1 * | 9/2014 | Walker | ................. | A61B 17/708 606/279 |
| 2014/0277206 A1 * | 9/2014 | Reitblat | ............. | A61B 17/7091 606/86 A |

* cited by examiner

*Primary Examiner* — Pedro Philogene
*Assistant Examiner* — Lynnsy Summitt

(57) ABSTRACT

Embodiments herein are generally directed to rod reduction clips that can efficiently attach to orthopedic fixation devices and reduce rods therein. Other embodiments herein are generally directed to coupling elements having removable extended tabs for use in orthopedic fixation devices.

12 Claims, 11 Drawing Sheets

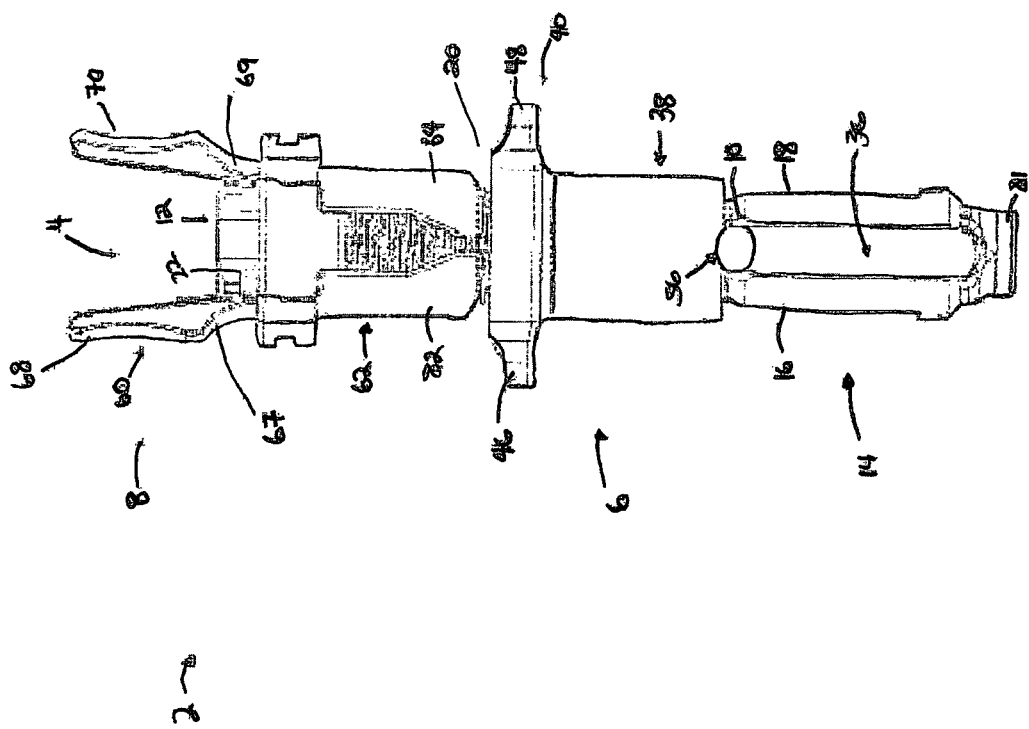

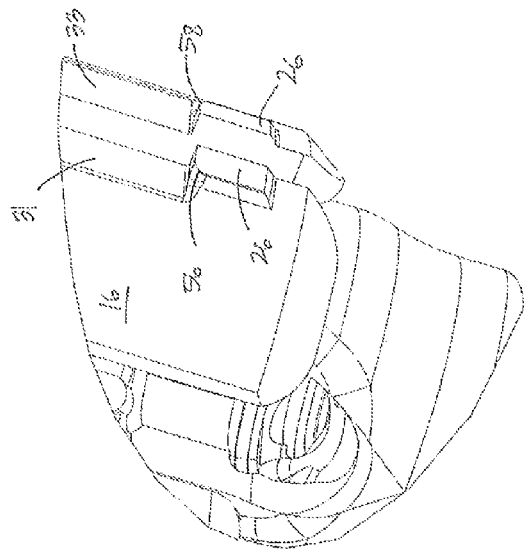
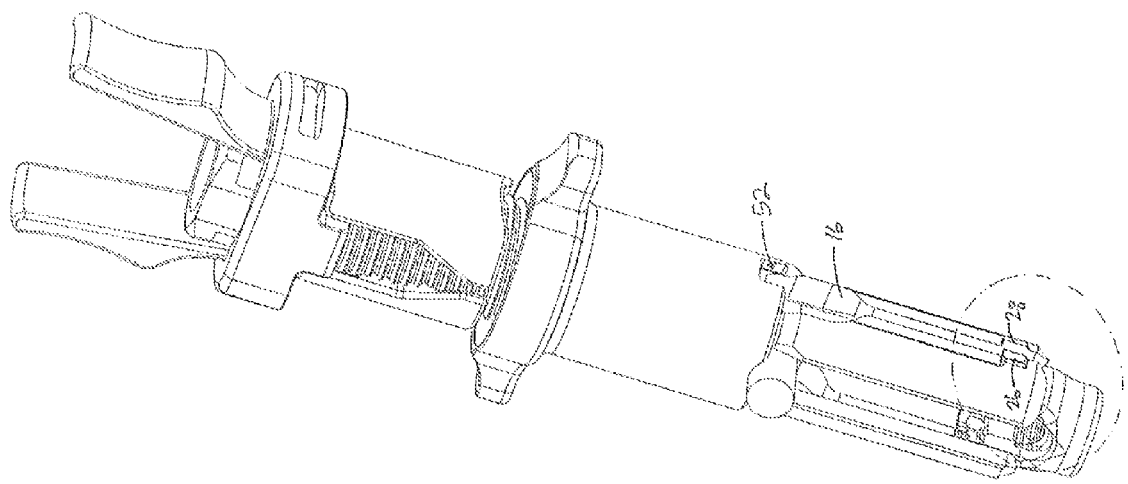

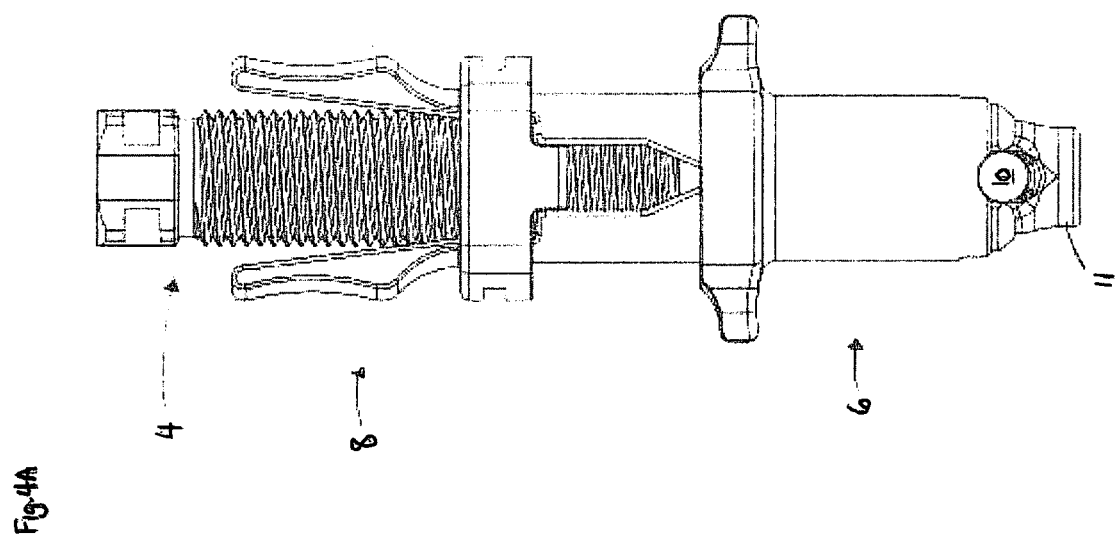

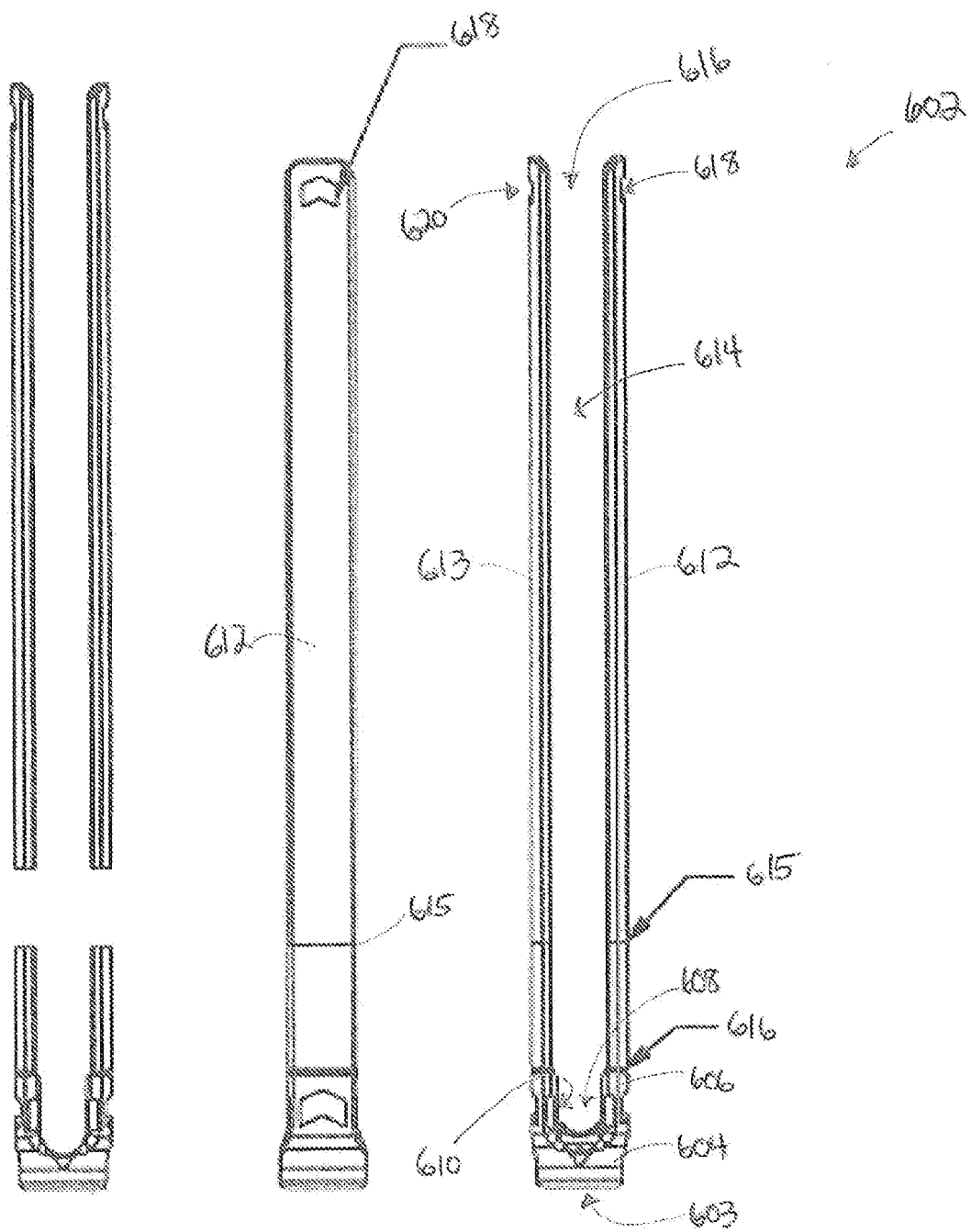

ORTHOPEDIC FIXATION DEVICES AND INSTRUMENTS FOR INSTALLATION THEREOF

FIELD OF THE INVENTION

The present invention relates to orthopedic fixation devices and instruments used to install these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of fixation devices to one or more vertebrae and connecting the devices to an elongate rod that generally extends in the direction of the axis of the spine.

Treatment for these spinal irregularities often involves using a system of fixation devices to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, a fixation device along with a vertical solid member can help restore spinal elements to a pain free situation, or at least may help reduce pain or prevent further injury to the spine.

Typically, fixation devices may include a bone fastener (e.g., bone screw, hook, etc.) for coupling the fixation device to vertebra. Fixation devices further may include a coupling element (e.g., a tulip element) for coupling the bone fastener to the vertical solid member (e.g., elongate rod). Clamp and/or wedge elements may be used to secure the bone fastener in the coupling element. A locking cap may be used to secure the rod in the coupling element.

In order for the elements of the fixation device to be secured, the rod may need to be seated firmly in the coupling element. A variety of methods may be used to maximize engagement between the rod and the coupling element. As one example, in an open surgery, a physician may be able to manually push the rod in contact with the coupling element. However, in other situations, such as in a minimally invasive or percutaneous procedure, it may be more difficult for the physician to view and/or maneuver the rod. In these types of situations, the physician may use a tool such as pliers, forceps, and/or a rod reducer to restore the rod to a proper position securely within the coupling element.

SUMMARY OF THE INVENTION

Some embodiments herein are directed to a reduction clip that can include a cannulated body comprising a proximal end and a distal end, the distal end comprising two tips extending therefrom and separated by a longitudinal channel; a rod reduction collar comprising an inner diameter configured to receive at least a portion of the cannulated body; and a reducer configured to fit around at least a portion of the cannulated body, proximal to the rod reduction collar.

Other embodiments herein are directed to a method of installing an orthopedic fixation device that can include providing a bone fastener disposed within a coupling element; providing a rod reduction clip disclosed herein, wherein the rod reduction collar is disposed around the cannulated body; placing the tips of the rod reduction clip around the coupling element, wherein the tips are in an open configuration; inserting a rod through the longitudinal channel of the rod reduction clip; distally sliding the rod reduction collar to push the tips into a closed configuration and secure the tips around the coupling element; attaching the reducer to the cannulated body; threading the reducer onto the cannulated body to engage the reducer with the rod reduction collar such that the rod reduction collar is pushed distally, thereby pushing the rod into the coupling element; inserting a cap member through the cannulated body; and securing the cap member in the coupling element.

Some embodiments herein are directed to a reduction clip that can include a cannulated body comprising a proximal portion and a distal portion, the distal portion comprising two tips separated by a longitudinal channel, wherein a first tip comprises a longitudinal slot defining a first edge and a second edge, with a first compressible prong disposed on the first edge and a second compressible prong disposed on the second edge; a lever comprising a proximal end and a distal end, the proximal end comprising a handle and the distal end comprising a first cam having a curved inner profile and being configured to receive the first and second compressible prongs, the lever further being configured to achieve a first orientation and a second orientation; and a reducer configured to fit within the cannulated body.

Other embodiments herein are directed to a method of installing an orthopedic fixation device that can include providing a bone fastener disposed within a coupling element; placing the tips of a rod reduction clip disclosed herein around the coupling element, wherein the lever is in the first orientation; inserting a rod through the longitudinal channel of the rod reduction clip; moving the lever from the first orientation to the second orientation such that the cam compresses the compressible prongs and the tips secure around the coupling element; moving the reducer distally into the cannulated body such that the reducer pushes the rod into the coupling element; inserting a cap member through the cannulated reducer and into the coupling element; and securing the cap member in the coupling element.

Some embodiments herein are directed to a reduction clip that can include a cannulated body comprising a proximal portion and a distal portion, the proximal portion comprising external threading and the distal portion comprising two tips extending therefrom, wherein the two tips are separated by a longitudinal channel; a compressor configured to fit around at least a portion of the cannulated body and configured to translate between an open position and a closed position; a rotating actuator configured to fit around at least a portion of the cannulated body at a position proximal to the compressor and comprising interior threading configured to mate with the exterior threading on the cannulated body; and a reducer configured to fit within the cannulated body.

Other embodiments herein are directed to a method of installing an orthopedic fixation device that can include providing a bone fastener disposed within a coupling element; placing the tips of a rod reduction clip disclosed herein around the coupling element, wherein the compressor is in the open position; inserting a rod through the longitudinal channel of the rod reduction clip; rotating the rotating actuator in a first direction to push the compressor distally into the closed position such that the compressor secures the tips around the coupling element; moving the reducer distally into the cannulated body such that the reducer pushes the rod into the coupling element; inserting a cap member through the cannulated reducer and into the coupling element; and securing the cap member into the coupling element.

Some embodiments herein are directed to a coupling element that can include a body, arms that extend from the body, and a removable extension tab extending from each arm, the arms defining a U-shaped channel configured to receive a rod, the removable extension tabs defining a lumen extending axially therethrough, and the body further comprising a bore there through and an interior surface disposed about the bore.

Other embodiments herein are directed to a method of installing an orthopedic fixation device that can include providing a bone fastener disposed within a coupling element, wherein the coupling element comprises a body, arms that extend from the body, and a removable extension tab extending from each arm, the arms defining a channel configured to receive a rod, the removable extension tabs defining a lumen extending axially therethrough, and the body further comprising a bore there through and an interior surface disposed about the bore; inserting a locking cap assembly into the lumen defined by the removable extension tabs; moving the locking cap assembly through the lumen until the locking cap assembly engages the arms of the coupling element; locking the locking cap assembly onto the coupling element; and removing the removable extension tabs.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1A is a side view of an embodiment of a rod reduction clip disclosed herein, wherein a rod reduction collar and reducer are in a proximal position;

FIG. 3A is a perspective view of an embodiment of a rod reduction clip disclosed herein, wherein a rod reduction collar and reducer are in a proximal position;

FIG. 3B is a close-up view of one section of the rod reduction clip illustrated in FIG. 3A;

FIG. 4A is a side view of an embodiment of a rod reduction clip disclosed herein, wherein a rod reduction collar and reducer are in a distal position;

FIG. 9A is a side view of an embodiment of a coupling element disclosed herein;

FIG. 9B is a side view of the embodiment illustrated in FIG. 9A and rotated by 90 degrees; and FIG. 9C is a side view of the embodiment illustrated in FIG. 9A.

DETAILED DESCRIPTION OF THE EMBODIMENTS

Figure 1B:
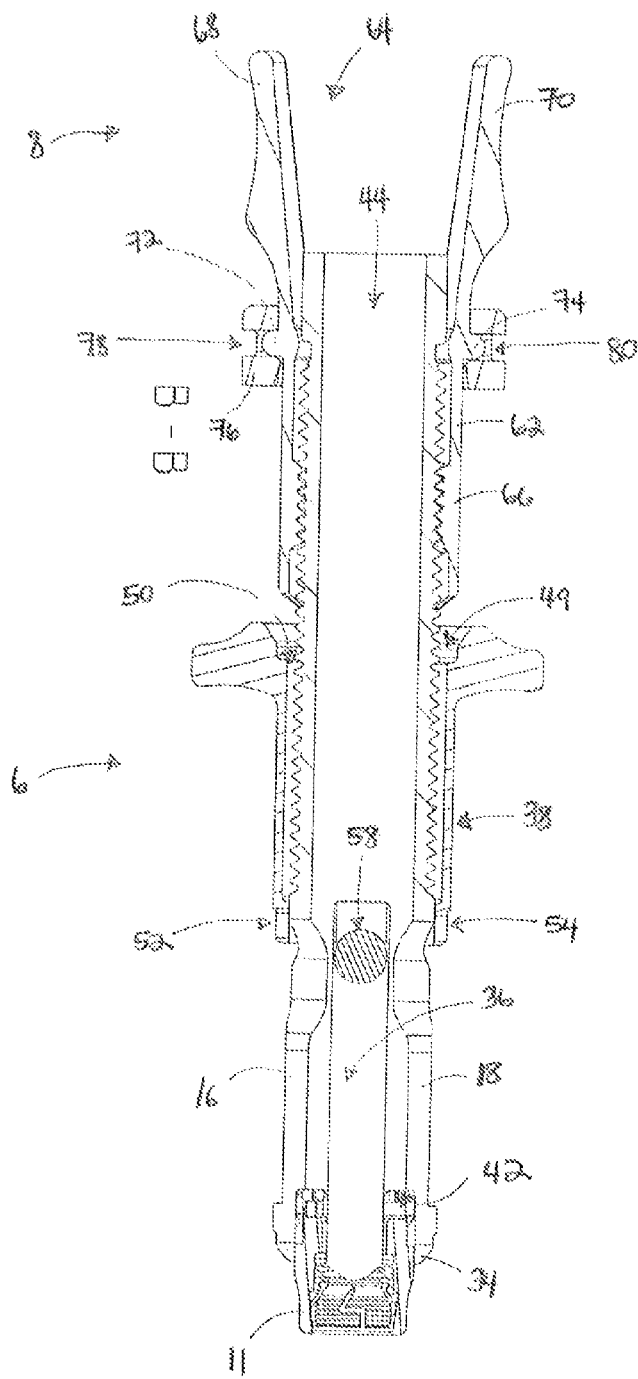
FIG. 1B is a cross-section of the side view of FIG. 1A.

A number of rod reduction assemblies may include both a clamping member and a reduction member, wherein the clamping member secures the assembly to an orthopedic fixation device and the reduction member moves an elongate member into contact with the orthopedic fixation device. The reduction of the rod can be a time consuming process due to the labor involved in using a rod reduction member (e.g., one that has to be downwardly threaded for extended lengths) in order to insert the rod into the orthopedic fixation device. In order to remove the rod reduction assembly, the reduction member may need to be retracted and the clamping member may also need to be released. Retraction of the reduction member can be a time consuming process due to the labor involved in having to unthread (e.g., upwardly thread) various components for extended lengths. In some instances, the separate performance of these steps may require a significant amount of time, particularly in a procedure where multiple orthopedic fixation devices and elongate members are involved.

Accordingly, disclosed herein are new and improved rod reduction assemblies (e.g., reduction clips) which can be removed from a fixation device without retracting the reduction member. Advantageously, in some embodiments, these reduction clips ease the insertion of a rod member into the fixation device and the removal of the reduction clips from a patient by providing sliding mechanisms in addition to threading mechanisms to ease the labor involved in performing these steps. Some embodiments are directed to a reduction clip that can include a cannulated body that includes at least two tips at a distal end, a compressor configured to compress the two tips, and a reducer configured to move axially along the cannulated body. Components of the reduction clips disclosed herein can be made of materials known to those skilled in the art, including metals (e.g., titanium), metal alloys, plastics (e.g., PEEK), and/or allograft. The components can also be machined and/or manufactured using techniques known to those skilled in the art.

Turning now to FIG. 1A, a side view of a reduction clip 2 is illustrated in accordance with embodiments described herein. As illustrated, the reduction clip 2 may include a cannulated body 4, a rod reduction collar 6, and a reducer 8. As will be discussed in more detail below, the rod reduction collar 6 may receive at least a portion of the cannulated body 4 therein. The reducer 8 may be applied (e.g., pinned and/or clipped) around the cannulated body 4 at a position proximal to the rod reduction collar 6. The rod reduction collar 6 and the reducer 8 may each be configured to translate between a proximal position (e.g., as illustrated in FIGS. 1A-3B) and a distal position (e.g., as illustrated in FIGS. 4A-6B) along the cannulated body 4. Application of force to the reducer 8 in the distal direction may have the effect of pushing the reducer 8 into the rod reduction collar 6, which may then push the rod reduction collar 6 into contact with a rod 10. Advantageously, the reduction clip 2 can push, persuade, and/or reduce the rod 10 into the proper and/or desired orientation within a coupling element 11 of an orthopedic fixation device (e.g., pedicle screw assembly). Any orthopedic fixation device known in the art can be used with the reduction clips disclosed herein. Some non-limiting examples include the orthopedic fixation devices disclosed in U.S. Publication No. 2013/0018428 to Harper et al., entitled "Orthopedic Fixation Devices and Methods of Installation Thereof," which is hereby incorporated by reference herein in its entirety for all purposes.

The cannulated body 4 will hereby be described in further detail. As shown in FIG. 1A-1B, the cannulated body 4 can include a proximal end 12 and a distal end 14. The cannulated body 4 can also include a cannula 44 extending therethrough, as illustrated in FIG. 1B. In some embodiments, the cannula 44 can have a smooth (e.g., non-threaded) interior surface. Advantageously, the cannula 44 can be sized and configured to receive one or more instruments therethrough. For example, the cannula 44 may be configured to receive an orthopedic fixation device or a portion thereof, such as a set screw.

The distal end 14 of the cannulated body 4 can include two tips 16, 18 extending therefrom. In some embodiments, the distal end 14 can include more than two tips extending therefrom (e.g., three or four tips). As illustrated in FIG. 1B, the distal end 14 can include a ledge 42. The ledge 42 can extend circumferentially around an interior surface of the distal end 14. Advantageously, the ledge 42 can abut an orthopedic fixation device or portion thereof. Thus, the orthopedic fixation device can be seated and/or captured within the cannulated body 4, with vertical motion of the orthopedic fixation device prevented beyond the ledge 42. In some embodiments, a distal-most end 34 of at least one tip can include a tapered exterior surface.

Figure 2A:
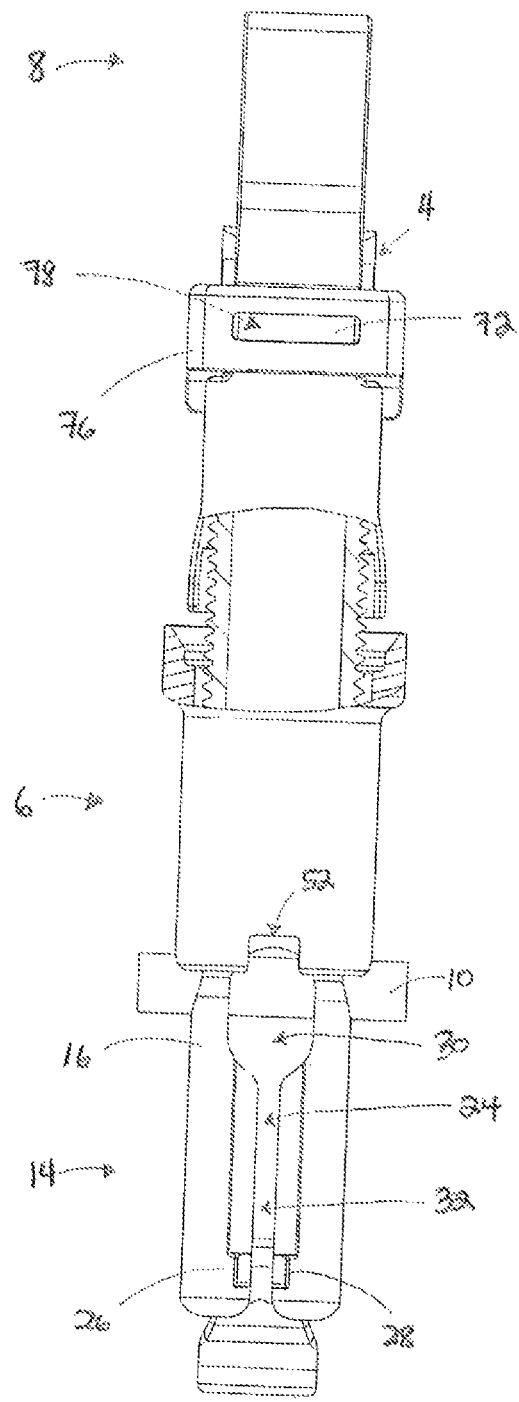
FIG. 2A is a side view of an embodiment of a rod reduction clip disclosed herein, in partial cross section, wherein a rod reduction collar and reducer are in a proximal position.

As illustrated in FIGS. 1A-1B, the two tips 16, 18 can be separated by a longitudinal channel 36. In some embodiments, the longitudinal channel 36 can be configured to receive the rod 10. A side view of the reduction clip 2 in partial cross section and rotated 90 degrees as compared to FIG. 1A is illustrated in FIG. 2A. As illustrated in FIG. 2A, one or more tips 16, 18 can be divided into two sections by a longitudinal slot 24. The sections may be referred to herein as tip sections. The slot 24 can have a variety of shapes. In some embodiments, the slot 24 can have a width that is greater at a proximal end than it is at a distal end. As illustrated in FIG. 2A, the slot 24 can have an oval-shaped proximal portion 30 and an elongated distal portion 32. In other embodiments, the proximal portion 30 of the slot 24 can be circular, elliptical, or rectangular.

As described further herein, the tips 16, 18 can be capable of a first, released (e.g., open and/or expanded) configuration, and a second, contracted (e.g., closed and/or compressed) configuration. In the released configuration, no external pressure may be applied to the tips 16, 18, and the tips and/or tip sections can be separated by a first distance. In the contracted configuration, an external pressure may be applied to the tips 16, 18, which can cause the tips and/or tip sections to move closer together. In the contracted configuration, the tips and/or tip sections may be separated by a second distance that is smaller than the first distance. These configurations can be achieved through a variety of mechanisms. For example, when external pressure is applied to the tips, the slot 24 may be compressed, thus bringing the tip sections closer together and transitioning the tips from the released configuration to the contracted configuration.

As illustrated in FIGS 2A, 3A, and 3B, the distal end of one or more tips 16, 18 can include radially-extending tabs 26, 28. In some embodiments each tip can include two radially-extending tabs. In other embodiments, a distal end of a tip 16, 18 can have one, two, three, four, or more radially-extending tabs. The tabs can be advantageously configured to mate with the rod reduction collar 6, as described further herein. As illustrated in FIG. 3B, the first radially-extending tab 26 can extend from a first tip edge 31 and the second radially-extending tab 28 can extend from a second tip edge 33. Each radially-extending tab can take on a variety of different shapes. For example, a radially-extending tab can be generally rectangular. As illustrated in FIG. 3B, each radially-extending tab 26, 28 can include a proximal curved edge 56, 58.

Figure 2B:
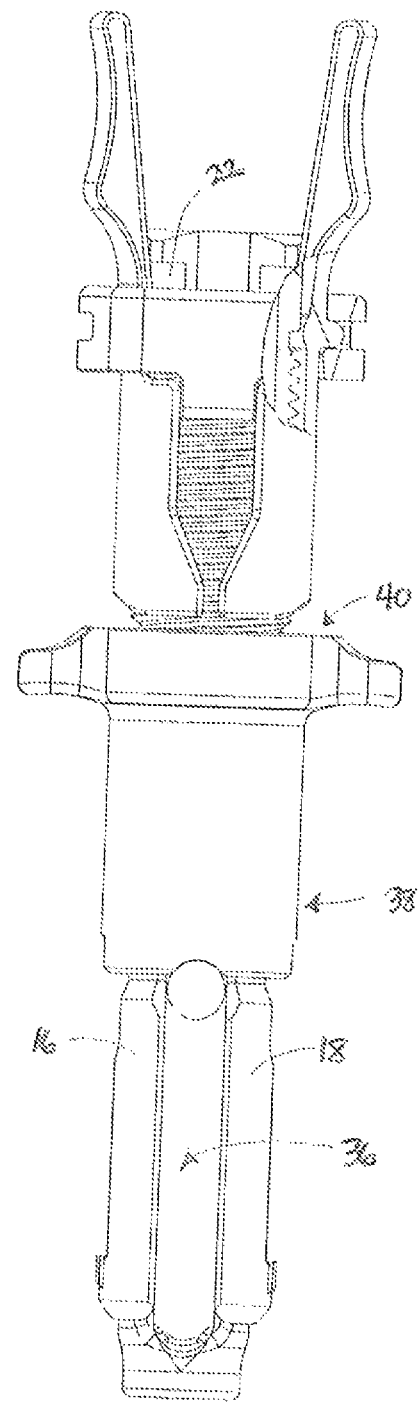
FIG. 2B is a side view of the embodiment illustrated in FIG. 2A rotated by 90 degrees, and also in partial cross section.

As illustrated in FIGS. 1A, 1B, and 2, the proximal end 12 can include an externally threaded portion 20. The proximal-most portion of the cannulated body 4 can advantageously include one or more tool-receiving windows 22, illustrated in FIG. 1A. In some embodiments, the proximal end 12 of the cannulated body 4 can be configured to receive, attach to, and/or mate with one or more tools, including but not limited to, a derotator, a torque-reducing apparatus, a wrench, and a removal driver.

The rod reduction collar 6 will be hereby described in further detail. The rod reduction collar 6 can include a proximal portion 40 and a distal portion 38. The rod reduction collar 6 can also include a cannula extending longitudinally therethrough. In some embodiments, the rod reduction collar 6 can have a smooth (e.g., non-threaded) interior surface. As illustrated in FIG. 1B, the cannula can be sized and configured to receive at least a portion of the cannulated body 4.

The proximal portion 40 of the rod reduction collar 6 can include a handle. The handle can advantageously be used to grip and/or to apply pressure to the rod reduction collar 6 and translate it along the cannulated body 4. For example, the handle can take the form of a cuff that extends circumferentially around the proximal portion 40. In some embodiments, the proximal portion 40 can include two or more handles. As illustrated in FIG. 1A, the proximal portion 40 can include two handles in the form of radially-extending ears 46, 48. The ears 46, 48 may be disposed evenly about the circumference of the proximal portion 40. For example, the ears 46, 48 may be disposed about 180 degrees apart from each other.

An inner surface of the proximal portion 40 of the rod reduction collar 6 can also include a depression 49 terminated by a ledge 50, as illustrated in FIG. 1B. The ledge 50 can extend circumferentially around the inner surface of the proximal portion 40. As described further herein, at least a portion of the reducer 8 can be received within the depression 49 of the rod reduction collar 6 and can abut and/or contact the ledge 50. The ledge 50 can advantageously prevent further linear movement of the reducer 8 through the rod reduction collar 6, and can allow the reducer 8 to push the rod reduction collar 6 and/or the rod 10 towards a receiving element (e.g., tulip head) of an orthopedic fixation device.

As illustrated in FIGS. 1B, 2A, and 3A, the distal portion 38 of the rod reduction collar 6 can include a recess 52. The recess 52 can be sized and configured to receive one or more radially-extending tabs disposed on the tips 16, 18 of the cannulated body 4. As described further herein, in some embodiments the recess 52 can be configured to receive both radially-extending tabs 26, 28. As illustrated in FIG. 1B, the rod reduction collar 6 can include a first recess 52 and a second recess 54, wherein the first recess 52 is configured to receive the radially-extending tabs from tip 16 and the second recess 54 is configured to receive the radially-extending tabs from tip 18.

As described further herein, the rod reduction collar 6 can be slideably engaged with the cannulated body 4. For example, the rod reduction collar 6 can slide over the cannulated body 4. When the rod reduction collar 6 slides over the tips 16, 18, the recess 52 can capture the tabs 26, 28 therein. In some embodiments, the width of the recess 52 is advantageously less than the distance across the radially-extending tabs 26, 28 and the gap therebetween. In these embodiments, the recess 52 can squeeze and/or compress the radially-extending tabs 26, 28, bringing the tip sections closer together from the released, expanded configuration to the contracted, compressed configuration. The curved surfaces 56, 58 can also advantageously help to direct the radially-extending tabs 26, 28 into the recess 52. When a coupling member 11 (e.g., tulip head), is disposed within the tips 16, 18, as illustrated in FIG. 1A, those skilled in the art may appreciate that bringing the tip sections closer together into the contracted configuration can have the effect of securing the coupling member 11 within the cannulated body 4.

As illustrated in FIGS. 1A-1B, the distal end of the rod reduction collar 6 can also include semicircular cut-outs 56, 58. The semicircular cut-outs 56, 58 can define a channel configured to receive the rod 10. Thus, when the rod reduction collar 6 slides over the cannulated body 4, as described herein, the rod reduction collar 6 can push, persuade, and/or reduce the rod into a proper and/or desired alignment within the coupling member 11.

The reducer 8 will be hereby described in further detail. As illustrated in FIG. 1A, the reducer 8 can include a proximal portion 60 and a distal portion 62. The reducer 8 can also include first and second halves 67, 69. The proximal portion 60 of the reducer 8 can include a first longitudinally extending member 68 extending proximally from the first half 67, and a second longitudinally extending member 70 extending proximally from the second half 69. The distal portion 62 of the reducer 8 can include a first sleeve member 82 extending distally from the first half 67 and a second sleeve member 84 extending distally from the second half 69. The longitudinally extending members 68, 70 can be used as a handle to apply and/or remove the reducer 8 to and/or from the cannulated body 4.

In some embodiments, the first and second halves 67, 69 can be connected by a hinge mechanism. In these embodiments, the reducer 8 may be referred to as a hinged reducer. In some embodiments, the hinge mechanism can include a rounded protrusion on a portion of the reducer 8, such as a longitudinally extending member, that pivots within another body, such as a fastening ring. As illustrated in FIG. 1B, the hinge mechanism can include rounded protrusions 72, 74 that extends transversely along a portion of the exterior surface of each of the longitudinally extending members 68, 70. As further illustrated in FIG. 1B, the rounded protrusions 72, 74 can be disposed within a fastening ring 76. The fastening ring 76 can be configured to fit around the proximal portion of the reducer 8. As illustrated in FIG. 1B, the fastening ring can include slots 78, 80 that are each configured to receive a rounded protrusion 72, 74. The rounded protrusions 72, 74 can be configured to pivot within the slots 78, 80. As illustrated in FIG. 2A, one or both slots (e.g., slot 78) can have a rectangular shape.

When the longitudinally extending members 68, 70 are squeezed together, the first and second sleeve members 82, 84 can be pulled apart to an open position. In this position, the reducer 8 can be applied to, clamped on, and/or placed around the cannulated body 4. The longitudinally extending members 68, 70 can then be released, causing the first and second sleeve members 82, 84 to be returned to their original (e.g., closed) position. In this position, the reducer 8 can be disposed and/or secured around the cannulated body 4. Those skilled in the art may appreciate that the hinge mechanism can also include a spring (not shown) or other device that causes the first and second sleeve members 82, 84 to automatically return to their original position once the longitudinally extending members 68, 70 are released.

As illustrated in FIG. 1B, the reducer 8 can also include a cannula 64 extending longitudinally therethrough. The cannulated body 4 can be received within the cannula 64 of the reducer 8. In some embodiments, the cannula 64 can include a smooth (e.g., non-threaded) inner surface. In other embodiments, the inner surface of the cannula 64 can include a smooth (e.g., non-threaded) portion and a threaded portion. As illustrated in FIG. 1B, the distal portion 62 of the reducer 8 can include an internally threaded section 66. The internally threaded section 66 can be configured to mate with the threaded portion of the cannulated body 4. In some embodiments, the internally threaded section 66 may extend along 50% or less of the length of the reducer 8. In other embodiments, the internally threaded section 66 may extend along 25% or less of the length of the reducer 8. In embodiments where the inner surface of the cannula 64 is not entirely threaded, the reducer 8 may advantageously be attached to and/or removed from the cannulated body 4 more quickly as compared to other embodiments where the inner surface of the cannula 64 is entirely and/or predominately threaded.

Embodiments herein are also directed to methods of installing an orthopedic fixation device. Any orthopedic fixation devices known in the art can be used with the reduction clips described herein. For example, the orthopedic fixation device can include a bone fastener (e.g., pedicle screw, hook, etc.), a coupling element (e.g., tulip head), an elongate member (e.g., rod), and a cap member (e.g., set screw). In some embodiments, the bone fastener can be disposed within the coupling element prior to application of the rod reduction clip. Those skilled in the art may appreciate that in some embodiments, the orthopedic fixation device can include other components, including but not limited to, a locking clamp assembly disposed between the coupling element and the bone fastener. In these embodiments, the bone fastener, locking clamp assembly, and coupling element may be assembled prior to application of the reduction clip.

The rod reduction clip may then be provided. At this point in the installation of the orthopedic fixation device, the rod reduction collar 6 may be disposed around the cannulated body 4. However, the reducer 8 may not yet be attached to the cannulated body 4. The tips 16, 18 of the rod reduction clip 2 may be placed around the coupling element 11 of the orthopedic fixation device. At this point, the tips 16, 18 may be in the open configuration. The rod 10 may then be inserted through the longitudinal channel 36 as illustrated in FIGS. 1A-3B, using any tools known in the art. The rod reduction collar 6 may then be slid distally along the tips 16, 18 of the cannulated body 4 to push the tips 16, 18 into the closed configuration, illustrated, for example in FIG. 6B. As described herein, the radially-extending tabs 26, 28 of the cannulated body 4 may be compressed into the recess 52 of the rod reduction collar 6. When the radially-extending tabs 26, 28 are compressed together, the tips and/or tip sections can also compress into the closed configuration, thereby securing the tips 16, 18 around the coupling element 11.

Subsequently, the reducer 8 can be attached to the cannulated body 4. In embodiments where a hinged reducer (e.g., reducer 8) is used, the first and second longitudinally extending members 68, 70 can be squeezed together to pull the first and second sleeve members 82, 84 apart from the closed position to the open position. Once in the open position, at least a portion of the cannulated body 4 can be positioned between and/or within the first and second sleeve members 82, 84. Subsequently, the first and second longitudinally extending members 68, 70 can be released to return the first and second sleeve members 82, 84 from the open position to the closed position, thereby securing the cannulated body 4 within the reducer 8.

Figure 4B:
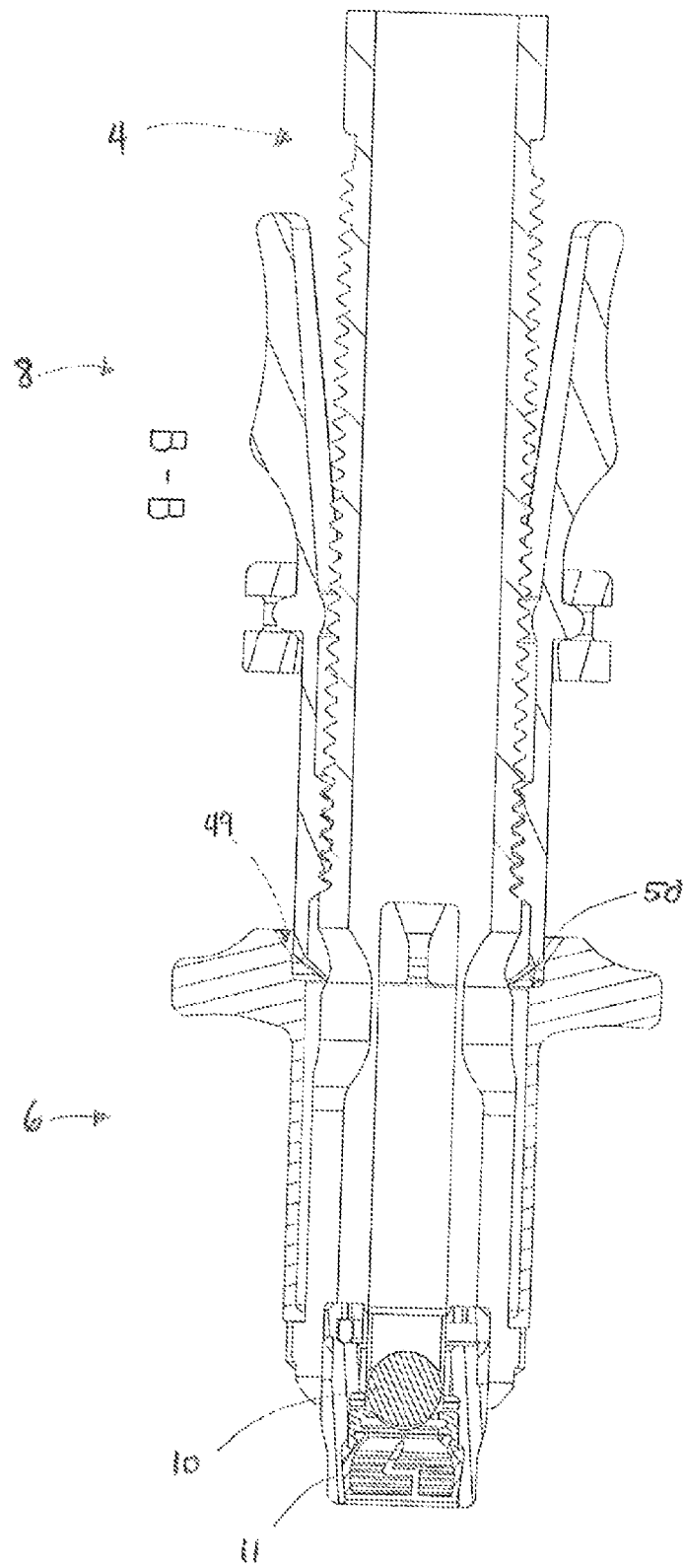
FIG. 4B is a cross-section of the side view of FIG. 4A.
Figure 5A:
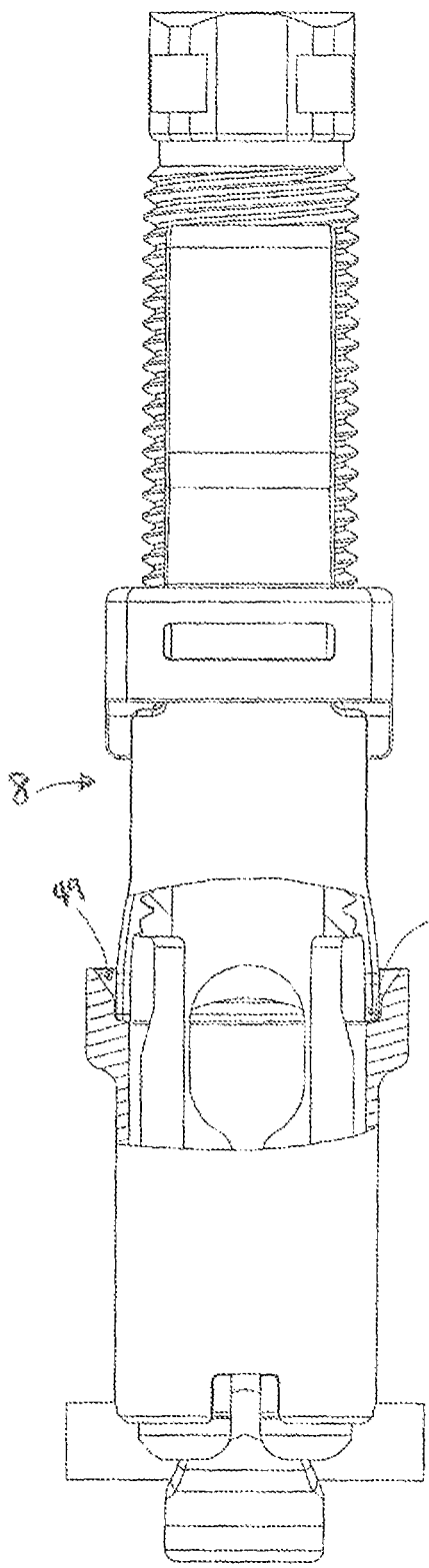
FIG. 5A is a side view of an embodiment of a rod reduction clip disclosed herein, in partial cross section, wherein a rod reduction collar and reducer are in a distal position.
Figure 5B:
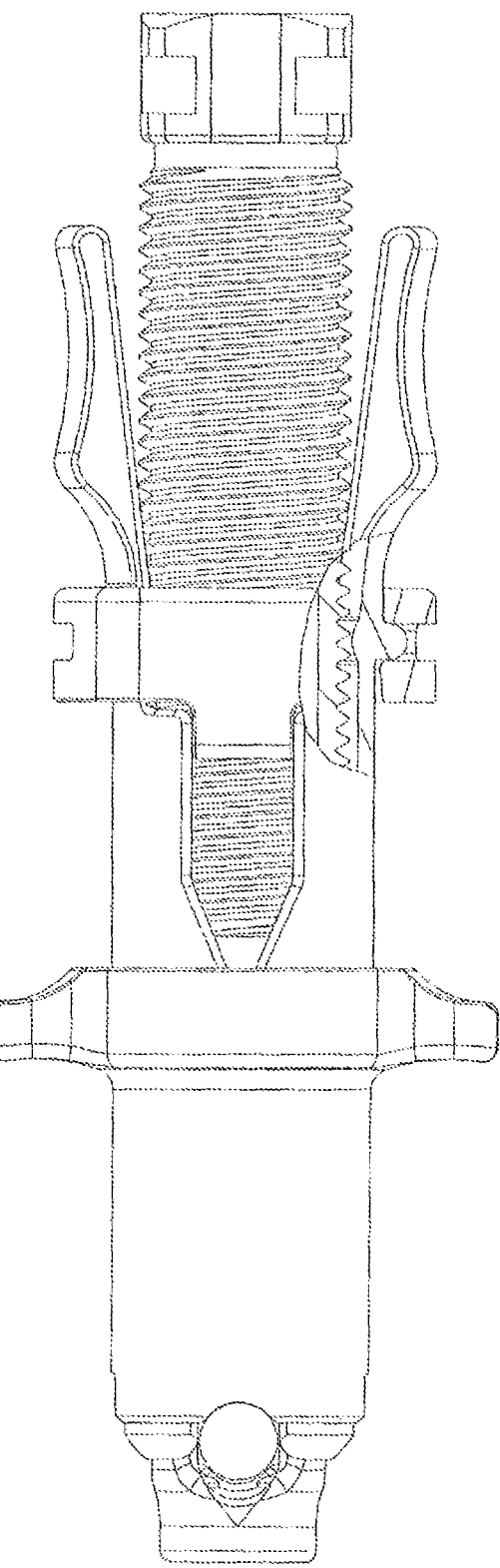
FIG. 5B is a side view of the embodiment illustrated in FIG. 5A rotated by 90 degrees, and also in partial cross section.
Figure 6A:
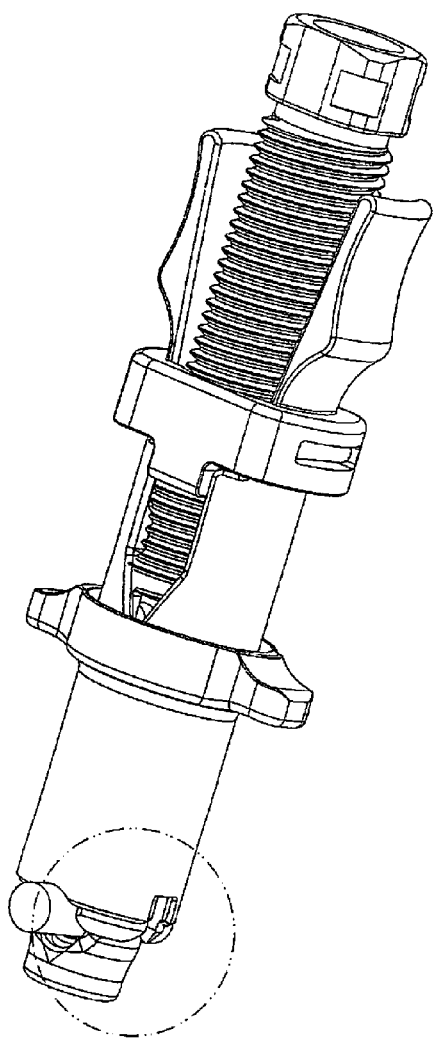
FIG. 6A is a perspective view of an embodiment of a rod reduction clip disclosed herein, wherein a rod reduction collar and reducer are in a distal position.
Figure 6B:
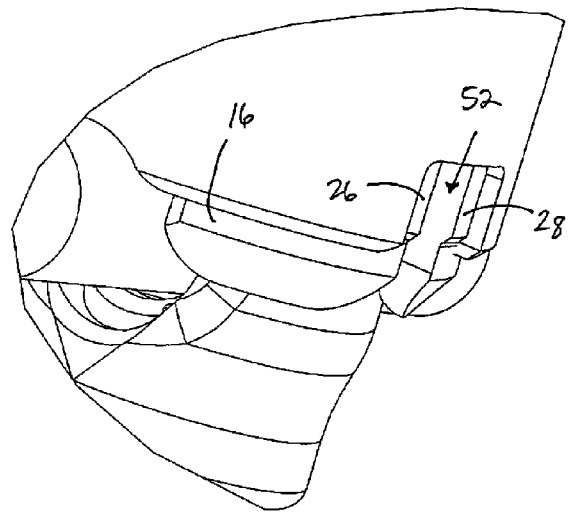
FIG. 6B is a close-up view of one section of the rod reduction clip illustrated in FIG. 6A.

Once the reducer 8 is attached (e.g., clipped and/or pinned via the hinge mechanism) to the cannulated body 4, it can be threaded distally onto the cannulated body 4. As mentioned herein, only a short section of the reducer 8 may be threaded (e.g., 50% or less). Advantageously, the threading step may not take as long as compared to methods utilizing other reducers that have predominantly or completely threaded interior cannulae. As it is being threaded on the cannulated body 4, the reducer 8 may translate distally until it engages the rod reduction collar 6. In some embodiments, the reducer 8 may be received within depression 49 and may contact the ledge 50 of the rod reduction collar 6, illustrated in FIGS. 4B and 5A. At that point, the force exerted on the reducer 8 may be transferred to the rod reduction collar 6, thereby pushing the rod reduction collar 6 distally. In turn, the rod reduction collar 6 may exert pressure on the rod 10, thereby pushing the rod into the coupling element 11, as illustrated in FIG. 4B. After the rod has been pushed, persuaded, and/or reduced into the proper and/or desired orientation within the coupling element, a cap member (not shown) may be inserted through the cannula 44 of the cannulated body 4 and secured within the coupling element 11.

Thereafter, the reduction clip 2 may be removed from the orthopedic fixation device. To do so, the reducer 8 may be unthreaded from the cannulated body 4 until it is released from the depression 49 of the rod reduction collar 6. Again, because only a short section of the reducer 8 may be threaded (e.g., 50% or less), the unthreading step may advantageously not take as long as compared to methods utilizing other reducers that may have predominantly or completely threaded interior cannulae. This time savings may be particularly significant in procedures that utilize multiple orthopedic fixation elements.

Subsequently, the reducer 8 may be removed from the cannulated body 4. In embodiments where a hinged reducer (e.g., reducer 8) is used, this step may include squeezing the first and second longitudinally extending members 68, 70 together to pull the first and second sleeve members 82, 84 apart from the closed position to the open position. Once in the open position, the reducer 8 can be removed from the cannulated body 4, and, the first and second longitudinally extending members 68, 70 can be released to return the first and second sleeve members 82, 84 from the open position to the closed position. The rod reduction collar 6 can then be slid proximally to release the tips and return them from the closed configuration to the open configuration, thereby releasing the coupling element. After the coupling element has been released, the reduction clip 2 can be removed from the orthopedic fixation device.

Figures 7A, 7B:
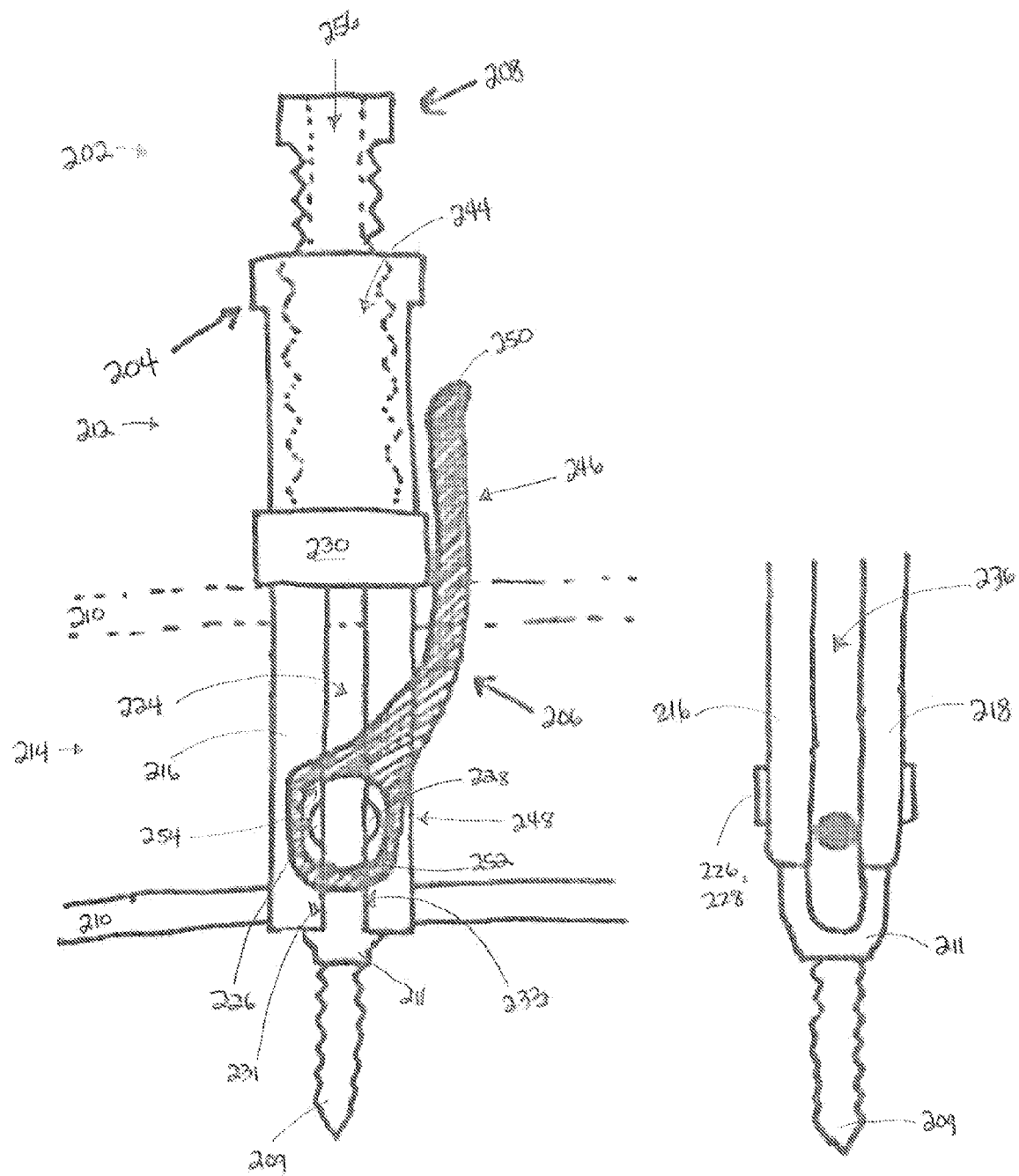
FIG. 7A is a side view, in partial cross section, of an embodiment of a rod reduction clip disclosed herein.
FIG. 7B is a partial side view of the embodiment illustrated in FIG. 7A and rotated by 90 degrees.

Referring to FIGS. 7A-B, an alternative embodiment of a reduction clip 202 is hereby described. Reduction clip 202 can include a cannulated body 204, a lever 206, and a reducer 208. Advantageously, the reduction clip 202 can push, persuade, and/or reduce a rod 210 into the proper and/or desired orientation within a coupling element 211 of an orthopedic fixation device (e.g., pedicle screw assembly). Any orthopedic fixation device known in the art can be used with the reduction clips disclosed herein, including those described in U.S. Publication No. 2013/0018428.

The cannulated body 204 will hereby be described in further detail. As illustrated in FIG. 7A, the cannulated body 204 can include a proximal end 212 and a distal end 214. The cannulated body 204 can also include a cannula 244 extending therethrough. In some embodiments, the cannula 244 can have a threaded interior surface. Advantageously, the cannula 244 can be sized and configured to receive one or more instruments therethrough. As illustrated in FIG. 7A, the reducer 208 can be received within the cannula 244.

As illustrated in FIG. 7B, the distal end 214 of the cannulated body 204 can include two tips 216, 218 extending therefrom. In some embodiments, the distal end 214 can include more than two tips extending therefrom (e.g., three or four tips). The two tips 216, 218 can be separated by a longitudinal channel 236. In some embodiments, the longitudinal channel 236 can be configured to receive the rod 210. As illustrated in FIG. 7A, tip 216 can be divided into two sections by a longitudinal slot 224. These sections may be referred to herein as tip sections. The slot can define a first edge 231 and a second edge 233, described further herein. The slot 224 can have a variety of shapes. As illustrated in FIG. 7A, the slot 224 can be rectangular. In other embodiments, the slot 224 can have a width that is greater at a proximal end than it is at a distal end. In yet other embodiments, the slot 224 can have an oval-shaped proximal portion and an elongated distal portion. In even other embodiments, the proximal portion of the slot can be circular or elliptical.

As described further herein, the tips 216, 218 can be capable of a first, released (e.g., open and/or expanded) configuration, and a second, contracted (e.g., closed and/or compressed) configuration. In the released configuration, no external pressure may be applied to the tips 216, 218, and the tips and/or tip sections can be separated by a first distance. In the contracted configuration, an external pressure may be applied to the tips 216, 218, which can cause the tips and/or tip sections to move closer together. In the contracted configuration, the tips and/or tip sections may be separated by a second distance that is smaller than the first distance. These configurations can be achieved through a variety of mechanisms. For example, when external pressure is applied to the tips, the slot 224 may be compressed, thus bringing the tip sections closer together and transitioning the tips from the released configuration to the contracted configuration.

As illustrated in FIG. 7A-B, the distal end of one or more tips 216, 218 can include one or more compressible prongs. In some embodiments, the compressible prongs may be referred to as radially-extending tabs, and may share some or all of the features of the radially-extending tabs described with regards to other embodiments of reduction clips discussed herein. In some embodiments, each tip can include two compressible prongs. In other embodiments, each tip can have one, two, three, four, or more compressible prongs. As illustrated in FIG. 7A, the distal end of tip 216 can include a first compressible prong 226 disposed along the first tip edge 231 and a second compressible prong 228 disposed along the second tip edge 233. In FIG. 7B, compressible prongs are also illustrated as extending from tip 218. Those skilled in the art may appreciate that the compressible prongs illustrated with respect to tip 216 can also be applied to tip 218. Each compressible prong can take on a variety of different shapes. For example, a compressible prong can be generally rectangular. In other embodiments, a compressible prong may include a curved edge. As illustrated in FIG. 7A, each compressible prong 226, 228 may be semicircular.

As illustrated in FIG. 7A, the proximal portion 212 can include an internally threaded cannula 244. The proximal-most portion of the cannulated body 204 can also include one or more tool-receiving windows. In some embodiments, the proximal portion 212 of the cannulated body 204 can be configured to receive and/or mate with one or more tools, including but not limited to, a derotator, a torque-reducing apparatus, a wrench, and a removal driver. The proximal portion 212 can also include a cuff 230. Although not illustrated, the cuff 230 can include two semi-circular cut-outs defining a channel to receive the rod 210. The cannulated body 204 can also include other features of the cannulated bodies of other embodiments of the reduction clips described herein. For example, cannulated body 204 can include a ledge extending circumferentially around an interior surface of the distal end 214, and that can abut an orthopedic fixation device or portion thereof (e.g., coupling element 211).

The lever 206 will be hereby described in further detail. The lever 206 can be rotatably and/or pivotably connected to at least one of the tips 216, 218. As illustrated in FIG. 7A, the lever 206 can include a proximal end 246 and a distal end 248. The proximal end 246 can include a handle 250. The distal end can include a first cam 252. The cam 252 can include an inner profile 254 that is curved. In some embodiments, the inner profile 254 can be ovular or elliptical. The inner profile 254 can include a major diameter and a minor diameter, wherein the major diameter is greater than the minor diameter. As illustrated in FIG. 7A, the cam 252 can be configured to receive the first and second compressible prongs 226, 228. In some embodiments, the distal end 248 can include a second cam (not shown) that can be configured to receive the first and second compressible prongs on tip 218.

The lever 206 can be configured to achieve a first, open orientation and a second, closed orientation. In the first orientation (not shown), the handle 250 can extend transversely from the cannulated body 204. Additionally, the compressible prongs 226, 228 may be aligned with the major diameter of the inner profile 254 of the cam 252. Accordingly, in the first orientation, the compressible prongs 226, 228 may not be compressed. In the second orientation, as illustrated in FIG. 7A, the handle 250 can extend longitudinally along the cannulated body 204. Additionally, the compressible prongs 226, 228 may be aligned with the minor axis of the cam 252. Due to the shorter distance of the minor axis, the compressible prongs 226, 228 may be compressed when in the second orientation.

When the lever 206 is in the first orientation and the compressible prongs 226, 228 are not compressed, the tip 216 may also be in the first, released (e.g., open and/or expanded) configuration. In this first configuration, the slot 224 may have a first width. When the lever 206 is in the second orientation and the compressible prongs 226, 228 are compressed, the pressure applied to the prongs may be transferred to the tip 216, such that the tip 216 may also be in the second, contract (e.g., closed and/or compressed) configuration. In this second orientation, the longitudinal slot 224 may have a second width. Because the prongs and tips are compressed in this orientation, the second width may be less than the first width, and the tips and/or tip sections may be squeezed together. Although described in terms of tip 216 as illustrated in FIG. 7A, those skilled in the art may understand that in some embodiments, tip 218 may also have compressible prongs that operate in a similar manner. In use, the lever 206 can be configured to move between the first orientation, where the tips and/or tip sections are separated, to the second position, where the tips and/or tip sections are moved together. Advantageously, a coupling element 211 can be secured within the cannulated body 204 between the tips 216, 218 when the lever 206 is in the second orientation. Conversely, the coupling element 211 can be released from the cannulated body 204 when the lever 206 is in the first orientation.

The reducer 208 will be hereby described in further detail. As illustrated in FIG. 7A, the reducer 208 can include external threading. The external threading can be configured to mate with the internal threading of the cannula 244 of the cannulated body 204. The reducer 208 can also have a lumen 256 extending longitudinally therethrough. In some embodiments, the lumen 256 can have a smooth (e.g., non-threaded) interior surface. Advantageously, the lumen 256 can be sized and configured to receive one or more instruments therethrough. For example, the lumen 256 may be configured to receive an orthopedic fixation device or a portion thereof, such as a cap member and/or a set screw. In some embodiments, the proximal-most end of the reducer 208 can also include a tool-receiving feature, such as a tool-receiving window, slot, and/or depression. In some embodiments, the proximal-most end of the reducer 208 can be configured to receive, attach to, and/or mate with one or more tools, including but not limited to, a derotator, a torque-reducing apparatus, a wrench, and a removal driver.

Other embodiments are directed to methods of installing an orthopedic fixation device using the reduction clip 202. As described herein, any orthopedic fixation devices known in the art can be used with reduction clip 202. In some embodiments, the orthopedic fixation device can include a bone fastener (e.g., pedicle screw, hook, etc.), a coupling element (e.g., tulip head), an elongate member (e.g., rod), and a cap member (e.g., set screw). As illustrated in FIGS. 7A-B, the orthopedic fixation device may include bone fastener 209, rod 210, and coupling element 211. In some embodiments, the bone fastener can be disposed within the coupling element prior to application of the rod reduction clip. Those skilled in the art may appreciate that in some embodiments, the orthopedic fixation device can include other components, including but not limited to, a locking clamp assembly disposed between the coupling element and the bone fastener. In these embodiments, the bone fastener, locking clamp assembly, and coupling element may be assembled prior to application of the reduction clip.

The rod reduction clip 202 may then be provided. At this point in the installation of the orthopedic device, the lever 206 may be in the first (e.g., open) orientation. The tips 216, 218 of the rod reduction clip 202 may be placed around coupling element 211. The tips 216, 218 may also be in the open configuration. The rod 210 may then be inserted through the longitudinal channel 36, as illustrated in FIGS. 7A-B, using any tools known in the art. The lever 206 may then be moved from the first orientation to the second orientation. As described herein, this action may result in the cam 252 compressing the compressible prongs 226, 228, causing the tips and/or tip sections to move closer together, thereby securing the tips around the coupling element 211. The reducer 208 may then be moved distally into the cannulated body 204. In some embodiments, the reducer 208 may be threaded into the cannulated body 204. In other embodiments, the reducer 208 may be slid into the cannulated body 204. As the reducer 208 moves distally, it may contact the rod 210, thereby pushing the rod 210 into the coupling element, as illustrated in FIG. 7A. After the rod 210 has been pushed, persuaded, and/or reduced into the proper and/or desired orientation within the coupling element, a cap member (not shown) may be inserted through the lumen 256 of the cannulated body 204 and secured within the coupling element 211.

Thereafter, the reduction clip 202 may be removed from the orthopedic fixation device. To do so, the lever 206 can be returned from the second orientation to the first orientation. In doing so, the cam 252 may disengage the compressible prongs 226, 228, thereby releasing the tips 216, 218 from around the coupling element 211. Advantageously, the reduction clip 202 may be removed from the orthopedic fixation device without regard to removal of the reducer 208 from the cannulated body 204. Accordingly, reduction clip 202 may be removed from an orthopedic fixation device more quickly than other reduction clips that require both disengagement of the tips and removal of the reducer in order for the reduction clip as a whole to be removed. This time savings may be particularly significant in procedures that utilize multiple orthopedic fixation elements.

Figure 8:
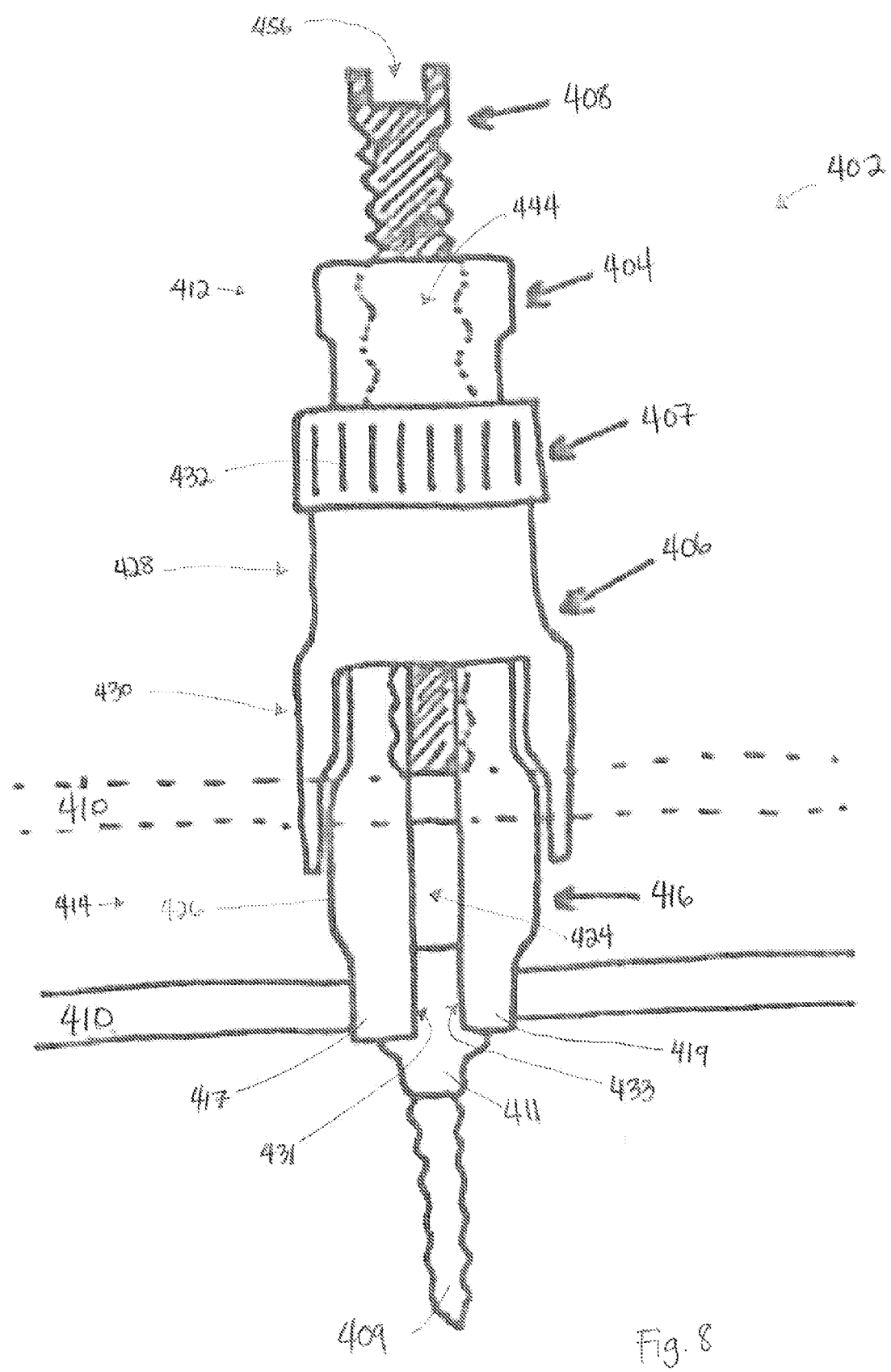
FIG. 8 is a side view of an embodiment of a rod reduction clip disclosed herein.

Referring to FIG. 8, an alternative embodiment of a reduction clip 402 is hereby described. Reduction clip 402 can include a cannulated body 404, a compressor 406, a rotating actuator 407, and a reducer 408. Advantageously, the reduction clip 402 can push, persuade, and/or reduce a rod 410 into the proper and/or desired orientation within a coupling element 411 of an orthopedic fixation device (e.g., pedicle screw assembly). Any orthopedic fixation device known in the art can be used with the reduction clips disclosed herein, including those described in U.S. Publication No. 2013/0018428.

The cannulated body 404 will hereby be described in further detail. As illustrated in FIG. 8, the cannulated body 404 can include a proximal end 412 and a distal end 414. The cannulated body 404 can also include a cannula 444 extending therethrough. In some embodiments, the cannula 444 can have a threaded interior surface. Advantageously, the cannula 444 can be sized and configured to receive one or more instruments therethrough. As illustrated in FIG. 8, the reducer 408 can be received within the cannula 444.

The distal end 414 of the cannulated body 404 can include two tips extending therefrom. Tip 416 is illustrated in FIG. 8. Although the second tip is not shown, those skilled in the art may appreciate that the second tip would be visible if the reduction clip 402 shown in FIG. 8 were rotated, for example, as in FIGS. 1A-B with respect to reduction clip 2. Those skilled in the art may also appreciate that the second tip can include some, if not all, of the same features as tip 416, and in some embodiments can be symmetrical and/or identical to tip 416. In other embodiments, the distal end 414 can include more than two tips extending therefrom (e.g., three or four tips).

The two tips can be separated by a longitudinal channel. In some embodiments, the longitudinal channel can be configured to receive the rod 410. As illustrated in FIG. 8, tip 416 can be divided into two sections 417, 419 by a longitudinal slot 424. These sections may be referred to herein as tip sections 417, 419. The slot 424 can define a first edge 431 and a second edge 433, described further herein. The slot 424 can have a variety of shapes. As illustrated in FIG. 8, the slot 424 can be rectangular. In other embodiments, the slot 424 can have a width that is greater at a proximal end than it is at a distal end. In yet other embodiments, the slot 424 can have an oval-shaped proximal portion and an elongated distal portion. In even other embodiments, the proximal portion of the slot can be circular or elliptical.

As illustrated in FIG. 8, the distal portion 414 of the cannulated body 404 can include a radially-expanded section 426. The radially-expanded section 426 can have an outer diameter that is greater than the outer diameter of the rest of the cannulated body 404. In some embodiments, the radially-expanded section 426 can include one or more bumps disposed on the tips and/or tip sections 417, 419.

As described further herein, the tips can be capable of a first, released (e.g., open and/or expanded) configuration, and a second, contracted (e.g., closed and/or compressed) configuration. In the released configuration, no external pressure may be applied to the tips, and the tips and/or tip sections 417, 419 can be separated by a first distance. In the contracted configuration, an external pressure may be applied to the tips, which can cause the tips and/or tip sections 417, 419 to move closer together. In the contracted configuration, the tips and/or tip sections 417, 419 may be separated by a second distance that is smaller than the first distance. These configurations can be achieved through a variety of mechanisms. For example, when external pressure is applied to the tips (e.g., at radially-expanded section 426), the slot 424 may be compressed, thus bringing the tip sections closer together and transitioning the tips from the released configuration to the contracted configuration.

As illustrated in FIG. 8, the proximal portion 412 can include an internally threaded cannula 444. The proximal-most portion of the cannulated body 404 can also include one or more tool-receiving windows. In some embodiments, the proximal portion 412 of the cannulated body 404 can be configured to receive and/or mate with one or more tools, including but not limited to, a derotator, a torque-reducing apparatus, a wrench, and a removal driver. The cannulated body 404 can advantageously also include other features of the cannulated bodies of other embodiments of the reduction clips described herein. For example, cannulated body 404 can include a ledge extending circumferentially around an interior surface of the distal end 414, and that can abut an orthopedic fixation device or portion thereof (e.g., coupling element 411). As another example, in some embodiments, the cannulated body 404 may include radially-extending tabs and/or compressible prongs that may be configured to engage with the compressor 406.

The compressor 406 will hereby be described in further detail. The compressor 406 can be configured to fit around at least a portion of the cannulated body 404. The compressor 406 can also be configured to slideably engage with the cannulated body 404. For example, the compressor 406 can have a smooth (e.g., non-threaded) inner surface. In some embodiments, the compressor 406 can slide along the cannulated body 404 between a proximal, open position and a distal, closed position, described in further detail herein.

The compressor 406 can include a proximal portion 428 and a distal portion 430. The distal portion 430 can include two semicircular cut-outs defining a channel to receive the rod 410. The proximal portion 428 can have a proximal inner diameter and the distal portion 430 can have a distal inner diameter. In some embodiments, the distal inner diameter and the proximal inner diameter can be equal. In these embodiments, the compressor 406 can have a constant inner diameter. In other embodiments, the distal inner diameter can be greater than the proximal inner diameter. In yet other embodiments, the compressor 406 can include a distal-most section having a distal-most inner diameter that is greater than both the distal inner diameter and the proximal inner diameter.

Advantageously, at least a portion of the compressor 406 can have an inner diameter than is less than the outer diameter portion of radially-expanded section 426 of the cannulated body 404. In, use, when in the proximal, open position, the compressor 406 (e.g., the portion having an inner diameter less than the outer diameter portion of radially-expanded section 426) may not be disposed over the radially-expanded section 426. In this position, the tips may be in the open, released configuration. When the compressor 406 (e.g., the portion having an inner diameter less than the outer diameter portion of radially-expanded section 426) slides over the radially-expanded section 426, it can capture the tips, squeezing them inward and causing them to transition from the released configuration to the contracted configuration. This configuration can be referred to herein as the distal, closed position of the compressor 406. Advantageously, the coupling element 411 can be secured within the cannulated body 404 between the tips when the compressor 406 is in the distal, closed position. Conversely, the coupling element 411 can be released from the cannulated body 404 when the compressor 406 slides proximately to return to the proximal, open position.

The rotating actuator 407 will hereby be described in further detail. The rotating actuator 407 can be configured to fit around at least a portion of the cannulated body 404. As illustrated in FIG. 8, the rotating actuator 407 can be located proximal to the compressor 406. In some embodiments, the rotating actuator 407 can be rotatably connected to the proximal end 428 of the compressor 406, for example, through the use of a tongue and groove joint. The rotating actuator can also include interior threading that is configured to mate with the external threading on the cannulated body 404. The rotating actuator 407 can further include a roughened outer surface 432, illustrated in FIG. 8. Advantageously, the roughened outer surface can assist a user with gripping and turning the rotating actuator 407. In use, the rotating actuator 407 can be used to move the compressor 406 between the open and closed positions. For example, when the rotating actuator 407 is rotated in a first direction (e.g., clockwise), it can be threaded distally onto the cannulated body 404, with the distally-directed force transferred to the compressor 406, causing the compressor 406 to slide distally. When the rotating actuator 407 is rotated in the opposite direction (e.g., counter-clockwise), it can be unthreaded, thus transferring the proximally-directed force to the compressor 406, causing the compressor 406 to slide proximally.

The reducer 408 will hereby be described in further detail. As illustrated in FIG. 8, the reducer 408 can include external threading. The external threading can be configured to mate with the internal threading of the cannula 444 of the cannulated body 404. The reducer 408 can also have a lumen 456 extending longitudinally therethrough. In some embodiments, the lumen 456 can have a smooth (e.g., non-threaded) interior surface. Advantageously, the lumen 456 can be sized and configured to receive one or more instruments therethrough. For example, the lumen 456 may be configured to receive an orthopedic fixation device or a portion thereof, such as a cap member and/or a set screw. In some embodiments, the proximal-most end of the reducer 408 can also include a tool-receiving feature, such as a tool-receiving window, slot, and/or depression. In some embodiments, the proximal-most end of the reducer 408 can be configured to receive, attach to, and/or mate with one or more tools, including but not limited to, a derotator, a torque-reducing apparatus, a wrench, and a removal driver.

Other embodiments herein are directed to methods of installing an orthopedic fixation device using the reduction clip 402. As described herein, any orthopedic fixation devices known in the art can be used with reduction clip 402. In some embodiments, the orthopedic fixation device can include a bone fastener (e.g., pedicle screw, hook, etc.), a coupling element (e.g., tulip head), an elongate member (e.g., rod), and a cap member (e.g., set screw). As illustrated in FIG. 8, the orthopedic fixation device may include bone fastener 409, rod 410, and coupling element 411. In some embodiments, the bone fastener can be disposed within the coupling element prior to application of the rod reduction clip. Those skilled in the art may appreciate that in some embodiments, the orthopedic fixation device can include other components, including but not limited to, a locking clamp assembly disposed between the coupling element and the bone fastener. In these embodiments, the bone fastener, locking clamp assembly, and coupling element may be assembled prior to application of the reduction clip.

The rod reduction clip 402 may then be provided. At this point in the installation of the orthopedic device, the compressor 406 may be in the open position and the tips may be in the open configuration. The tips of the rod reduction clip 402 may then be placed around the coupling element 411. The rod 410 may then be inserted through the longitudinal channel, using any tools known in the art. The rotating actuator 407 may then be rotated in a first direction to push the compressor 406 distally such that the compressor 406 secures the tips around the coupling element 411. This can be accomplished by sliding the compressor 406 from the open position to the closed position, as discussed herein. The reducer 408 may then be moved distally into the cannulated body 404. In some embodiments, the reducer 408 may be threaded into the cannulated body 404. In other embodiments, the reducer 408 may be slid into the cannulated body 404. As the reducer 408 moves distally, it may contact the rod 410, thereby pushing the rod 410 into the coupling element, as illustrated in FIG. 8. After the rod 410 has been pushed, persuaded, and/or reduced into the proper and/or desired orientation within the coupling element, a cap member (not shown) may be inserted through the lumen 456 of the cannulated body 404 and secured within the coupling element 411.

Thereafter, the reduction clip 402 may be removed from the orthopedic fixation device. To do so, the rotating actuator 407 may be rotated in a second direction opposite the first direction. This can have the effect of pulling the compressor 406 proximally from the closed position to the open position, thereby releasing the tips from around the coupling element 411. Advantageously, the reduction clip 402 may be removed from the orthopedic fixation device without regard to removal of the reducer 408 from the cannulated body 404. Accordingly, reduction clip 402 may be removed from an orthopedic fixation device more quickly than other reduction clips that require both disengagement of the tips and removal of the reducer in order for the reduction clip as a whole to be removed. This time savings may be particularly significant in procedures that utilize multiple orthopedic fixation elements.

Various methods may be used to install an orthopedic fixation device into a vertebral area. In an open surgery, the vertebral bodies may be exposed via an incision that can be several inches long. Musculature and other tissue may also be incised and retracted during this process to expose the vertebrae. A surgeon may then be able to insert the components of the fixation device. In other instances, an orthopedic fixation device may be installed using a minimally invasive surgical (MIS) technique. In this type of surgery, the components of the fixation device may be inserted through small incisions, with visualization supplemented through the use of fluoroscopy and/or an endoscope. In these procedures, a tube or sleeve may be placed in the incision, with components such as the coupling element and/or the bone fastener being passed therethrough to the vertebrae.

Although MIS techniques may result in reduced trauma to surrounding tissue as compared to traditional surgical techniques, it is noted that the use of a tube or sleeve can increase the diameter of the orthopedic fixation device elements, thereby somewhat reducing the benefits of the technique. Accordingly, disclosed herein are new and improved orthopedic fixation devices that do not require a separate delivery device.

Some embodiments herein are directed to a coupling element 602, illustrated in FIGS. 9A-C. In some embodiments, the coupling element 602 may be referred to as a tulip element or a tulip head. Those skilled in the art may appreciate that the coupling element 602 can be a part of an orthopedic fixation device, such as those disclosed in U.S. Publication No. 2013/0018428. Additionally, the coupling element 602 may include one or more features of the coupling elements disclosed therein.

The coupling element 602 can include body 604, arms 606 that extend upwardly from the body, and removable extension tabs 612, 613 as illustrated in FIG. 9A. The body 604 can include a bore 603 therethrough and an interior surface disposed around the bore. The arms can 606 can define a U-shaped channel 608 sized to receive a rod (not shown). Each of the arms 606 can include an interior surface 610. The interior surface 610 can be configured to engage a locking cap assembly (e.g., set screw). In some embodiments, the interior surface 610 can have a threaded portion within which a set screw can be threaded. In other embodiments, the interior surface 610 can include one or more slots and/or recesses configured to receive a tab and/or other protuberance from a locking cap assembly.

The removable extension tabs 612, 613 can be separated by a longitudinal channel 614. The longitudinal channel 614 can be configured to receive the rod. The removable extension tabs 612, 613 can also define a lumen 616 that extends axially through the coupling element 602. Advantageously, the removable extension tabs 612, 613 can be easily removed and/or disconnected from the arms 606. In some embodiments, this can be accomplished by incorporating a structural weakness between the arms 606 and the removable extension tabs 612, 613. As illustrated in FIG. 9A, the coupling element 602 can also include a break point 616 between the removable extension tabs 612, 613 and the arms 606. In other embodiments, the coupling element 602 can include a groove between the removable extension tabs 612, 613 and the arms 606.

In some embodiments, the removable extension tabs 612, 613 can each be machined in one piece along with the rest of the coupling element 602. In other embodiments, the removable extension tabs 612, 613 or a portion thereof can be machined separately. As illustrated in FIGS. 9A-C, the removable extension tabs 612, 613 can be divided into two sections by a weld 615. In these embodiments, a proximal portion of the removable extension tabs 612, 613 can be welded onto a distal portion of the removable extension tabs. In yet other embodiments, the removable extension tabs 612, 613 may not be divided into sections.

Those skilled in the art may appreciate that the removable extension tabs 612, 613 can be configured for use as a sleeve through which instruments can be inserted. Accordingly, the removable extension tabs 612, 613 may advantageously include one or more features to accept instrumentation. For example, as illustrated in FIGS. 9A-B, the proximal end of the removable extension tab 612, 613 can include tool-engaging windows 618, 620. Instruments that the tool-engaging windows 618, 620 can be configured to receive, accept, and/or engage can include, but are not limited to, drivers, rod reducers, rod pushers, anti-torque devices, distractors, persuaders, pliers, clamps, and/or wrenches. Those skilled in the art may appreciate that the instruments that can engage with the removable extension tabs 612, 613 may be used in various steps of an installation procedure, including but not limited to, screw insertion, rod reduction, and tab removal.

Those skilled in the art may appreciate that, traditionally, the installation of an orthopedic fixation device can require the use of a separate sleeve through which various components of the device, as well as associated instrumentation, may be passed. These sleeves may be attached to the orthopedic fixation device via prongs, protrusions, and the like, which can increase the diameter of the assembly, thereby causing additional damage to the installation site. For example, the increased diameter can require a relatively larger incision, which can in turn lead to more tissue damage and increased recovery time for a patient.

Advantageously, the inclusion of removable extension tabs 612, 613 of orthopedic fixation device 602 may eliminate the need for a separate sleeve. Additionally, the removable extension tabs 612, 613 may have an outer diameter that is not greater than an outer diameter of the body 604 of the coupling element 602. In some embodiments, the outer diameter of the removable tabs 612, 613 may be less than the outer diameter of the body 604 of the coupling element 602. Accordingly, in use, an orthopedic fixation device assembly that includes coupling element 602 instead of a separate sleeve can have a diameter that is less than that of an orthopedic fixation device assembly that includes a traditional coupling element (e.g., without removable extension tabs) and a separate sleeve. In some embodiments, an orthopedic fixation device assembly that includes coupling element 602 can have a diameter that is from about 5% to about 50% less than a diameter of an orthopedic fixation device assembly that utilizes a separate sleeve. In other embodiments, an orthopedic fixation device assembly that includes coupling element 602 can have a diameter that is from about 10% to about 40% less than a diameter of an orthopedic fixation device assembly that utilizes a separate sleeve. As mentioned herein, this reduction in diameter can advantageously result in a smaller incision, less damage to the installation site, and/or reduced recovery time.

As mentioned herein, the coupling element 602 can be part of an orthopedic fixation device, including but not limited to those disclosed in U.S. Publication No. 2013/0018428. Accordingly, some embodiments herein are directed to an orthopedic fixation device that can include coupling element 602, a bone fastener, a locking clamp assembly, and a locking cap assembly. Also disclosed herein are methods of installing an orthopedic fixation device that includes coupling element 602. Although generally described with reference to the orthopedic fixation devices disclosed in U.S. Publication No. 2013/0018428, it may be appreciated that the coupling element 602 can be used in place of other coupling elements (e.g., tulip elements or tulip heads) known in the art.

The method can include providing a bone fastener disposed within coupling element 602. In some embodiments, when a locking clamp assembly is to be disposed between the coupling element and the bone fastener, this step can include inserting a locking clamp assembly into the bore 603 in the coupling element, wherein the locking clamp assembly comprises a wedge element and a clamp element secured to the wedge element. This step can further include moving the locking clamp assembly through the bore 603 in the coupling element 602 until a recessed surface on the wedge element engages a protuberance on an interior surface of the coupling element 602 to secure the locking clamp assembly in the coupling element 602; inserting a head of the bone fastener into the clamp element such that the clamp element engages the head; and moving the wedge element downward past the protuberance on the interior surface of the coupling element 602 such that the exterior surfaces of the clamp element engage the interior surface of the coupling element 602 forcing the clamp element to clamp onto the head of the bone fastener to secure the bone fastener in the coupling element 602.

In embodiments where the orthopedic fixation device is installed within a vertebra, the bone fastener can then be inserted into the vertebra. Advantageously, a separate sleeve is not needed to perform this step, as mentioned previously herein. Optionally, a rod can then be inserted through the longitudinal channel 614 and/or the U-shaped channel 608. Advantageously, the longitudinal channel 614 can guide and/or reduce the rod into the desired orientation. A locking cap assembly (e.g., set screw) can then be inserted into the lumen 616 and moved therethrough until the locking cap assembly engages the arms 606. The locking cap assembly can then be locked onto the coupling element 602, for example, by threading, clicking, and/or snapping the locking cap assembly into the coupling element 602. Once the locking cap assembly is secured in the coupling element 602, the removable extension tabs 612, 613 can be removed. The removable extension tabs 612, 613 can be removed using a variety of tools and/or methods known in the art. In some embodiments, the tabs can be bent and broken off at the break point 616. Any suitable tool can be used, including but not limited to pliers or clamps.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A spinal system comprising:
   a cannulated body comprising a proximal end and a distal end, the distal end comprising two tips extending therefrom and separated by a longitudinal channel;
   a rod reduction collar comprising an inner diameter configured to receive at least a portion of the cannulated body; and
   a reducer configured to fit around at least a portion of the cannulated body, proximal to the rod reduction collar
   wherein the reducer comprises first and second halves connected by a hinge mechanism
   wherein a proximal portion of the reducer comprises first and second longitudinally extending members extending from each of the first and second halves, and a distal portion of the reducer comprises first and second sleeve members extending from each of the first and second halves; wherein the reducer engages with the cannulated body proximal to the rod reduction collar.

2. The system of claim 1, wherein a distal portion of the rod reduction collar comprises a recess configured to receive a radially-extending tab disposed on a distal end of at least one tip.

3. The system of claim 1, wherein the rod reduction collar is slideably engaged with the cannulated body.

4. The system of claim 1, wherein the cannulated body comprises a tool-receiving window.

5. The system of claim 1, further comprising a derotation apparatus attached to a proximal portion of the cannulated body.

6. The system of claim 1, wherein a proximal portion of the rod reduction collar comprises a handle in the form of a cuff.

7. A spinal system comprising:
   a cannulated body comprising a proximal end and a distal end, the distal end comprising two tips extending therefrom and separated by a longitudinal channel;
   a rod reduction collar comprising an inner diameter configured to receive at least a portion of the cannulated body; and
   a reducer configured to fit around at least a portion of the cannulated body, proximal to the rod reduction collar
   wherein the reducer comprises first and second halves connected by a hinge mechanism, wherein a proximal portion of the reducer comprises first and second longitudinally extending members extending from each of the first and second halves,
   a rounded protrusion extending transversely along a portion of an exterior surface of each of the longitudinally extending members; and
   a fastening ring configured to fit around the proximal portion of the reducer, the fastening ring having two slots that are each configured to receive one of the rounded protrusions, and within which each of the rounded protrusions is configured to pivot.

8. The system of claim 7, wherein a distal portion of the rod reduction collar comprises a recess configured to receive a radially-extending tab disposed on a distal end of at least one tip.

9. The system of claim 7, wherein the rod reduction collar is slideably engaged with the cannulated body.

10. The system of claim 7, wherein the cannulated body comprises a tool-receiving window.

11. The system of claim 7, further comprising a derotation apparatus attached to a proximal portion of the cannulated body.

12. The system of claim 7, wherein a proximal portion of the rod reduction collar comprises a handle in the form of a cuff.

* * * * *